United States Patent [19]

Gorman

[11] 4,161,526

[45] Jul. 17, 1979

[54] ZINC SALT PREVENTION OR REMOVAL OF DISCOLORATION IN PYRITHIONE, PYRITHIONE SALT AND DIPYRITHIONE COMPOSITIONS

[75] Inventor: William G. Gorman, East Greenbush, N.Y.

[73] Assignee: Sterling Drug Inc., New York, N.Y.

[21] Appl. No.: 926,293

[22] Filed: Jul. 20, 1978

[51] Int. Cl.$^2$ .................. A61K 31/555; A61K 31/44; A61K 33/30

[52] U.S. Cl. .................................. 424/245; 424/145; 424/263

[58] Field of Search .................. 424/145, 245, 263

[56] References Cited

U.S. PATENT DOCUMENTS

| | | | |
|---|---|---|---|
| 2,809,971 | 10/1957 | Bernstein et al. | 424/245 |
| 3,236,733 | 2/1966 | Karsten et al. | 424/245 |
| 3,412,033 | 11/1968 | Karsten et al. | 252/107 |
| 3,785,985 | 1/1974 | Grand | 424/245 |
| 3,890,434 | 6/1975 | Weisse et al. | 424/70 |
| 3,940,482 | 2/1976 | Grand | 424/245 |
| 4,039,312 | 8/1977 | Patru | 424/245 |
| 4,067,878 | 1/1978 | Miller et al. | 424/245 |

FOREIGN PATENT DOCUMENTS

92881/77 8/1977 Japan.

*Primary Examiner*—Albert T. Meyers
*Assistant Examiner*—D. W. Robinson
*Attorney, Agent, or Firm*—Theodore C. Miller; B. Woodrow Wyatt

[57] ABSTRACT

Pyrithione, pyrithione salt or dipyrithione compositions containing the zinc salt of an organic or inorganic acid, zinc hydroxide or zinc oxide or a mixture thereof for prevention or removal of discoloration in said compositions, and the process of preventing such discoloration, are disclosed.

6 Claims, No Drawings

ZINC SALT PREVENTION OR REMOVAL OF DISCOLORATION IN PYRITHIONE, PYRITHIONE SALT AND DIPYRITHIONE COMPOSITIONS

BACKGROUND OF THE INVENTION

1. Field of the Invention

This invention relates to prevention or removal of discoloration in pyrithione, pyrithione salt and dipyrithione compositions.

2. Description of the Prior Art

The closest prior art is believed to be U.S. Pat. No. 3,890,434, issued June 17, 1975, which describes alkaline earth metal (calcium, magnesium, barium and strontium) salt adducts of dipyrithione and shampoo formulations thereof. U.S. Pat. No. 3,236,733, issued Feb. 22, 1966, describes antidandruff shampoo compositions containing pyrithione, pyrithione salts and dipyrithione. U.S. Pat. No. 3,412,033, issued Nov. 19, 1968, describes germicidal skin cleansing compositions containing pyrithione, pyrithione salts and dipyrithione.

An important problem of pyrithione, pyrithione salt and dipyrithione compositions is discoloration (usually to gray, green, blue, or purple colors). Consumer dissatisfaction and economic loss can result from such discoloration. It is believed that the discoloration results from formation of iron pyrithione from unwanted traces of iron in the compositions, which may be introduced through contaminated raw materials or contact with iron during product manufacture, handling or storage. The present invention is a solution to this problem.

3. Prior Publication

Japanese patent application disclosure No. 92881/77, published Aug. 4, 1977 (application No. 9113/76, filed Jan. 30, 1976), describes a process for preparing an aqueous suspension which comprises stabilizing zinc pyrithione in the presence of zinc oxide as a stabilizing agent. The present invention was made before Aug. 4, 1977.

SUMMARY OF THE INVENTION

In a composition of matter aspect the invention is a pyrithione, pyrithione salt or dipyrithione composition containing from about 0.01 percent to about 1 percent of the zinc salt of an organic or inorganic acid, zinc hydroxide or zinc oxide or a mixture thereof.

In a process aspect the invention is the process for preventing or removing discoloration in a pyrithione, pyrithione salt or dipyrithione composition which comprises adding to the composition from about 0.01 percent to about 1 percent of the zinc salt of an organic or inorganic acid, zinc hydroxide or zinc oxide or a mixture thereof.

DETAILED DESCRIPTION OF THE INVENTION INCLUSIVE OF THE PREFERRED EMBODIMENTS

The antimicrobial properties of pyrithione, pyrithione salts, especially zinc pyrithione, and dipyrithione are well-known and are applied in antimicrobial compositions, for example, skin cleansing compositions and antidandruff shampoo compositions. Another application is that in which the pyrithione, pyrithione salt or dipyrithione is used as a preservative against the growth of micro-organisms in compositions, for example, cosmetic compositions.

In carrying out the present invention the zinc salt of any organic or inorganic acid compatible with the pyrithione, pyrithione salt or dipyrithione composition may be used, although readily and economically available zinc salts are preferred, for example, zinc acetate, zinc chloride and zinc sulfate. Hydrates and ammoniates of zinc salts may also be used. Zinc oxide and zinc hydroxide, which is a hydrated form of zinc oxide, are also useful and are readily available.

The essence of the present invention can be shown by simple laboratory tests. In one such test a white to off-white aqueous suspension of zinc pyrithione was prepared. Addition of a small quantity of ferric chloride produced a purple discoloration. Addition of zinc chloride to the suspension rapidly changed the color from purple to cream yellow. In another test zinc chloride (0.5 percent) was added to an aqueous dipyrithione emulsion which had developed a gray color, whereupon the gray color was removed and the original color of the emulsion was restored.

EXAMPLE

The following example is a skin cleansing composition containing zinc pyrithione as an antimicrobial agent and/or preservative.

| Ingredient | Percent by Weight |
|---|---|
| Cocamidopropyl Betaine | 10.0xx |
| Sodium Laureth Sulfate (29%) | 7.14x |
| Sodium Laureth Sulfate (59%) | 5.10x |
| Petrolatum | 5.00x |
| PEG-75 | 2.50x |
| PEG-150 Distearate | 2.00x |
| Magnesium Aluminum Silicate | 2.00x |
| PVP | 1.00x |
| Petrolatum, Lanolin and Lanolin Alcohol | 0.500 |
| PEG-8 Stearate | 0.500 |
| Zinc Pyrithione | 0.100 |
| Water to make | 100.0xx |

The composition of the foregoing example developed an undesirable gray color. A portion whitened extremely well upon addition of 0.1 percent of zinc sulfate, whereas addition of 0.1 percent of calcium chloride to another portion produced no significant whitening. Addition of 0.1 percent of aluminum sulfate or 0.1 percent of mangesium chloride to portions of a similar composition also produced no significant whitening. However, addition of 0.1 percent of zinc oxide to a similar composition produced considerable whitening and a much better looking product.

I claim:

1. A white to cream yellow pyrithione, pyrithione salt or dipyrithione composition for application to skin or hair containing from about 0.01 percent to about 1 percent of the zinc salt of an organic carboxylic or inorganic acid, zinc hydroxide or zinc oxide or a mixture thereof effective in preventing or removing discoloration caused by formation of a colored pyrithione, pyrithione salt or dipyrithione contaminant in said composition.

2. A composition according to claim 1 wherein the pyrithione salt is zinc pyrithione.

3. A composition according to claim 2 wherein the zinc salt is zinc sulfate.

4. The process for preventing or removing discoloration in a white to cream yellow pyrithione, pyrithione salt or dipyrithione composition for application to skin or hair which comprises adding to the composition from about 0.01 percent to about 1 percent of a zinc salt of an organic carboxylic or inorganic acid, zinc hydroxide or zinc oxide or a mixture thereof effective in preventing or removing discoloration caused by formation of a colored pyrithione, pyrithione salt or dipyrithione contaminant in said composition.

5. The process according to claim 4 wherein the pyrithione salt is zinc pyrithione.

6. The process according to claim 5 wherein the zinc salt is zinc sulfate.

* * * * *